United States Patent
Wei et al.

(10) Patent No.: US 9,541,527 B1
(45) Date of Patent: Jan. 10, 2017

(54) MAGNETIC DEVICE WITH THREE-DIMENSIONAL WAVE STRUCTURE AND APPLICATION FOR BIOMEDICAL DETECTION

(71) Applicant: NATIONAL TSING HUA UNIVERSITY, Hsinchu (TW)

(72) Inventors: Zung-Hang Wei, Hsinchu (TW); Jen-Hwa Hsu, Taipei (TW); Ching-Ray Chang, Taipei (TW); Hao-Ting Huang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/924,214

(22) Filed: Oct. 27, 2015

(30) Foreign Application Priority Data

Sep. 11, 2015 (TW) .............................. 104130203 A (51) Int. Cl.
| | |
|---|---|
| *G01N 27/00* | (2006.01) |
| *G01N 25/18* | (2006.01) |
| *G01N 25/08* | (2006.01) |
| *B01L 3/00* | (2006.01) |
| *G01N 27/74* | (2006.01) |
| *G01R 33/09* | (2006.01) |
| *G01R 33/12* | (2006.01) |

(52) U.S. Cl.
CPC ........... *G01N 27/745* (2013.01); *G01R 33/091* (2013.01); *G01R 33/096* (2013.01); *G01R 33/1276* (2013.01)

(58) Field of Classification Search
CPC ......... G01N 15/06; G01N 33/00; G01N 33/48
USPC ........ 422/50, 68.1, 502, 503, 82.01; 436/43, 436/149
See application file for complete search history.

(56) References Cited

U.S. PATENT DOCUMENTS

| | | | |
|---|---|---|---|
| 2008/0053695 A1* | 3/2008 | Choi .............................. | 174/390 |
| 2014/0204463 A1* | 7/2014 | Harada et al. ................ | 359/565 |
| 2014/0246608 A1* | 9/2014 | Liu et al. .................... | 250/515.1 |

* cited by examiner

*Primary Examiner* — Brian J Sines
(74) *Attorney, Agent, or Firm* — Muncy, Geissler, Olds & Lowe, P.C.

(57) ABSTRACT

A magnetic device with a three-dimensional wave structure is provided, which contains magnetic elements and a signal receiver. The magnetic element is nano/micron structure with magnetic anisotropy. The magnetic element is formed on a substrate with three-dimensional wave structure. When a magnetic substance approaches to the magnetic element, the magnetic substance produces a corresponding magnetoresistance signal for the magnetic element. Through the measurement of the magnetoresistance of the three-dimensional wave structure, and the presence or absence of the magnetic substance can be detected. An external magnetic field is used to change the magnetization configuration of the three-dimensional wave structure to capture the magnetic substance by adsorbing the magnetic substance to a magnetic pole of the three-dimensional wave structure.

10 Claims, 7 Drawing Sheets

MAGNETIC DEVICE WITH THREE-DIMENSIONAL WAVE STRUCTURE AND APPLICATION FOR BIOMEDICAL DETECTION

CROSS-REFERENCE TO RELATED APPLICATION

This application claims priority from Taiwan Patent Application No. 104130203, filed on Sep. 11, 2015, in the Taiwan Intellectual Property Office, the content of which is hereby incorporated by reference in their entirety for all purposes.

BACKGROUND OF THE INVENTION

1. Field of the Invention

This application relates to a magnetic device with a three-dimensional wave structure which is applied to detect the variations of the magnetic fields of the magnetic substances by measuring the variations of the magnetoresistance of the three-dimensional wave structure. In addition, the magnetization configuration can be changed by an external magnetic field so as to capture the magnetic substances adsorbed to the magnetic pole region of the three-dimensional wave structure. The present device aims to detect, capture, separate, collect, position, and count the magnetically-tagged biomolecules and the application for the biomedical detection.

2. Description of the Related Art

Recently, with the increasing emphasis on the biotechnology and the growth market of the global biomedical industry depending on the diagnostic medicine and physiology, home physiological monitoring, action health care and implantable medical systems and so on, the productivity and needs of the biotechnology increases gradually. Focus of the technology-related biomedical science wants nothing more than tasks of the biomedical materials, such as detection, capture, analysis and so on. The development of the biomedical detection is the most important. However, most of the conventional biomedical detection systems are applied the optical detection method to detect the cells or the biomolecules tagged by fluorescent substance or quantum dots. The detected solutions for the optical detection method, however, must be transparent and non-turbid and have as few impurities as possible, such that the misjudgment possibility of equipment, which may result from that the light signal from the to-be-detected substance is blocked by the impurities, can be reduced. Furthermore, the commonly used quantum dots may be slightly toxic, and are not suitable for the medical testing of cells.

After the surface of the magnetic nano-particles is modified, the biological toxicity still exists but is within a tolerable range. Hence, the modified magnetic nano-particles are usually applied in the field of biomedical science to process magnetic tagging. Furthermore, the cells or the biomolecules which are magnetically-tagged may indirectly achieve the objective of detecting the cells or the biomolecules through measuring the magnetic field emitted by the magnetic nano-particles. Similarly, the purification and collection of the biomolecules can be implemented through manipulating an external magnetic field.

Currently, most of the sensors applied to detect the magnetic substances are the element with two dimensional flat surfaces, and the applied range is therefore limited. Although the conventional technique has disclosed that a plurality of flat surface elements are assembled to form a three-dimensional magnetic detector, manufacturing process and the determining process of the necessary detection elements are more complicated.

In conclusion, the inventor of the present invention has been mulling the aforementioned technical problems over, and then designs a magnetic device with a three-dimensional wave structure and an application for the biomedical detection which is applied to overcome the existing drawbacks so as to promote the industrial applicability.

SUMMARY OF THE INVENTION

In view of the foregoing technical problem, the objective of the present invention provides a magnetic device with three-dimensional wave structure and an application for biomedical detection which applies the special three-dimensional wave structure to detect the change of the magnetoresistance thereof. Consequently, the magnetic field emitted by the magnetic substance can be detected, the presence and absence of the magnetic substances are able to be detected, and the efficiency and precision of the detection can be promoted greatly.

In view of the foregoing technical problem, the objective of the present invention provides a magnetic device with three-dimensional wave structure and an application for biomedical detection which cooperates with a micro-fluid channel system to detect the cells or the biomolecules which are magnetically-tagged so as to increase the efficiency and precision of detecting the specific biologic sample.

In view of the foregoing technical problem, the objective of the present invention provides a magnetic device with three-dimensional wave structure and an application for biomedical detection which is able to change the magnetization configuration of the three-dimensional wave structure by controlling the magnetic field such that the magnetic substance, the magnetically-tagged cells, or the magnetically-tagged biomolecules is able to be adsorbed to the magnetic pole of the three-dimensional wave structure so as to achieve the objective of capturing the magnetic substances, cells or biomolecules.

In view of the foregoing technical problem, the objective of the present invention provides a magnetic device with three-dimensional wave structure and an application for biomedical detection which is able to adsorb and capture the magnetic substances through the modulation of an external magnetic field. In addition, the magnetic device may further combine the washing function of the micro-fluid to separate the magnetic substances from the non-magnetic substances. Consequently, objectives of purification and collection are thereby achieved.

In view of the foregoing technical problem, the objective of the present invention provides a magnetic device with a three-dimensional wave structure and an application for biomedical detection which further applies the modulation of the external magnetic field to change the magnetization configuration of the three-dimensional wave structure, such that the various cells are distributed at the tops and gaps of the three-dimensional wave structure so as to arrange the cells in a pattern.

According to the preceding objective, the present invention provides a magnetic device with the three-dimensional wave structure which may include at least one magnetic element comprising a nano/micro structure having magnetic anisotropy and the at least one magnetic element prepared on a substrate with a three-dimensional wave structure; a magnetic substance correspondingly producing a magnetoresistance signal to the at least one magnetic element when the magnetic substance approaches the at least one magnetic element, and a signal receiver electrically connected to the at least one magnetic element to receive the magnetoresistance signal corresponding to the at least one magnetic element.

Preferably, the magnetic device with the three-dimensional wave structure may further include a magnetic field controller transmitting a modulation signal to control an external magnetic field.

Preferably, a magnetic pole region may be formed in a three-dimensional wave structure of the at least one magnetic element by the three-dimensional wave structure according to the modulation signal, and the magnetic pole region may capture and/or fixes the magnetic substance.

Preferably, the magnetic device with the three-dimensional wave structure may include a microfluid generator providing a microfluid, and when the magnetic substance is fixed to the magnetic pole region, the external magnetic field may perform a magnetic field modulation and cooperate with a washing function of the microfluid so as to be served as a magnetic substance separating system.

Preferably, the external magnetic field may be applied in an arbitrary axial direction based on an actual requirement to reinforce detection intensity and a detection freedom of the magnetoresistance signal.

Preferably, the modulation signal may change an applied direction of the external magnetic field to change a magnetization configuration of the at least one magnetic element so as to arrange the magnetic substance in a pattern.

Preferably, the magnetic device with a three-dimensional wave structure may further include a flow channel unit connected thereto to detect the magnetic substance flowing through the flow channel unit so as to be served as a magnetic counting system.

Preferably, the signal receiver may be served as a position detector and; or a path tracker of the magnetic substance according to different magnetoresistance signals corresponding to the at least one magnetic element when the at least one magnetic element is arranged in a matrix.

Preferably, the magnetic substance may include a magnetically-tagged biomolecule, a magnetic particle, a magnetic cell, a magnetic molecular structure, a magnetic fluid or a combination thereof.

Preferably, the nano/micro structure may include a linear structure, a thin film structure, a ring structure, a circular structure, an Antidot, an elliptic structure, a spin valve structure or a combination thereof.

The main objective of the present invention provides a magnetic device with a three-dimensional wave structure and an application for biomedical detection and the provided magnetic device with the three-dimensional wave structure and the application for biomedical detection may have the following advantages.

1. The detection method is simple. The presence and absence of the magnetic substances and the variation thereof are able to be detected only through the magnetoresistance signal of the measurement element.

2. The multi-axial detection. The magnetic substances are able to be detected no matter the magnetoresistance signal is in X, Y or Z-axis direction. Hence, the measurement has a great freedom in detecting.

3. The capture of the magnetic substance. Under the control of the modulation of the magnetic field, the bent position of the three-dimensional structure may have magnetic pole which is applied to capture and/or fix the magnetic substances, magnetically-tagged cells or biomolecules to perform the process of separation or purification.

4. The pattern arrangement. By the cooperation of the three-dimensional wave structure and the change of the magnetization configuration, the various cells or biomolecules are able to be respectively arranged at the tops and gaps of the three-dimensional wave structure so as to achieve the objective of arranging the cells or biomolecules in patterns.

5. The separation of magnetic substances. Under the control of the modulation of the external magnetic field, the non-magnetic substances, non-magnetically-tagged cells or biomolecules adsorbed on the magnetic pole can be separated from the magnetic substances, magnetically-tagged cells or biomolecules after being washed by the micro-fluid.

6. The magnetic biomedical counter. As the magnetic element is capable of detecting the presence of the magnetic substances, magnetically-tagged cells or biomolecules, the magnetic detection element is able to be applied to count the amount of the cells or biomolecules flowing through the flow channel unit.

7. The position detector and/or a path tracker of the magnetic substance. A plurality of magnetic elements is able to be arranged in a matrix by the position detector and/or a path tracker. When the magnetic substances fall in the matrix, the position of the magnetic substance can be detected through the magnetoresistance signal of each three-dimensional wave structure. Hence, the present device is able to be served as the position detector and/or a path tracker of the magnetic substance.

With these and other objects, advantages, and features of the invention that may become hereinafter apparent, the nature of the invention may be more clearly understood by reference to the detailed description of the invention, the embodiments and to the several drawings herein.

BRIEF DESCRIPTION OF THE DRAWINGS

Hereinafter, embodiments of the present invention will be described in detail with reference to the accompanying drawings so that those skilled in the art to which the present invention pertains can realize the present invention, wherein.

DETAILED DESCRIPTION OF THE PREFERRED EMBODIMENTS

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

The exemplary embodiments of the present invention will be understood more fully from the detailed description given below and from the accompanying drawings of various embodiments of the invention, which, however, should not be taken to limit the invention to the specific embodiments, but are for explanation and understanding only.

The magnetic detection technology is referred to control of the movement of the magnetic substances so as further to control or detects the magnetically-tagged object in a complex system through the modulation of an external magnetic field. Besides, the magnetic detection method provides non-invasive and non-contact properties. In the practical measurement, the magnetic detection technology has advantages of simple measuring steps, higher sensitivity and so on, compared with the optical or electrical detection method.

The magnetoresistance effect applies the variation of the external magnetic field to change the resistance of the magnetic substances, such that the internal magnetization process of the magnetic substances can be obtained by measuring the variation of the magnetoresistance. The magnetoresistance effect may be divided into the following types according to the diversity of the properties and compositions of the magnetic materials. Ordinary magnetoresistance (OMR), Anisotropic magnetoresistance (AMR), Giant magnetoresinace, (GMR), Colossal magnetoresistance, (CMR), and Tunnel magnetoresistance (TMR).

The present invention, however, applies the measurement technique of magnetoresistance to measure the relative magnetization angle of the magnetic measurement element and the magnetoresistance value corresponding to various magnetization angles. Besides, the present invention applies the magnetoresistance signals of the anisotropic magentoresistance to perform the determination and analysis, so as to effectively simplify the process of determining and the analyzing the magnetoresistance data.

Figure 1:
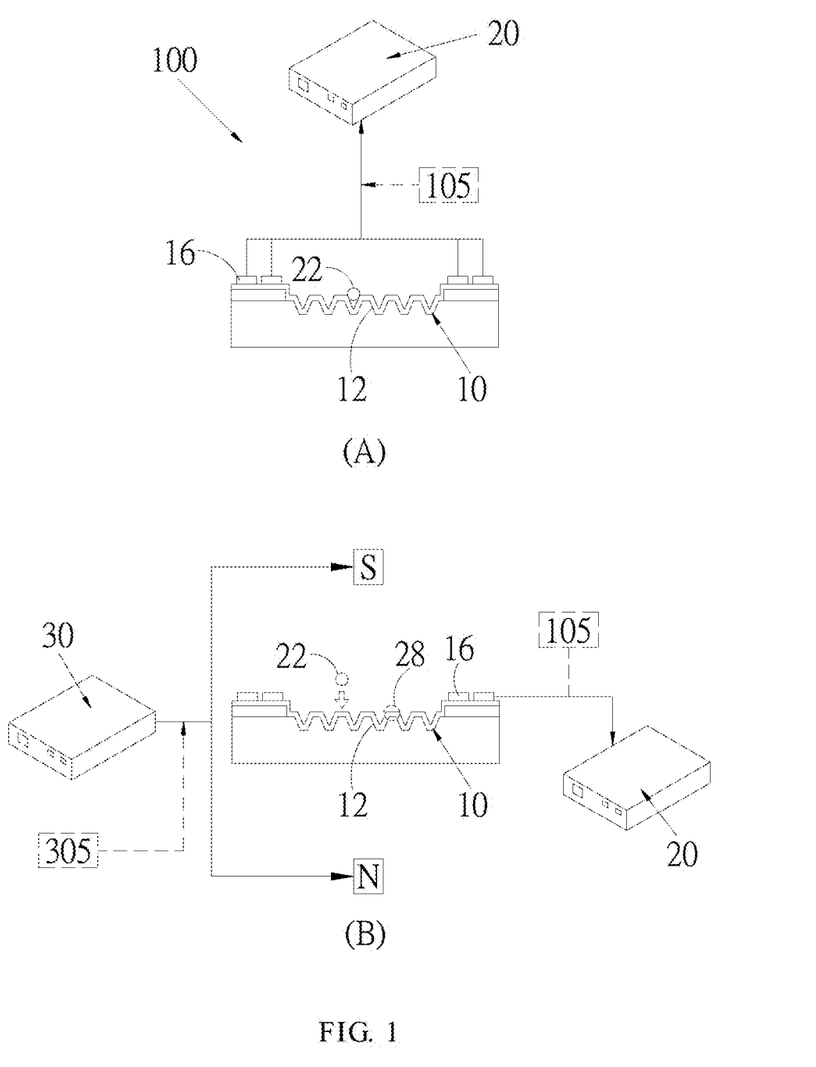
FIG. 1 is a schematic diagram of a magnetic device with a three-dimensional wave structure of the present invention.

Please refer to FIG. 1 which is a schematic diagram of a magnetic device with a three-dimensional wave structure of the present invention. As shown in FIG. 1, a magnetic device 100 with a three-dimensional wave structure includes a magnetic element 10 and a signal receiver 20. The magnetic element 10 includes a nano/micro structure having magnetic anisotropy and is prepared on a substrate with a three-dimensional wave structure 12. The magnetic material is deposited within the region of the substrate with the three-dimensional wave structure 12 by the vapor deposition.

In practice, the nano/micro structure of the magnetic element 10 may include a linear structure, a thin film structure, a ring structure, a circular structure, an Antidot, an elliptic structure, a spin valve structure or a combination thereof to increase the sensitivity of the detection of a magnetic substance 22. The magnetic substance 22 includes a magnetically-tagged biomolecule, a magnetic particle, a magnetic cell, a magnetic molecular structure, a magnetic fluid or a combination thereof.

In this embodiment, the magnetic element 10 may include ferromagnetic material, such as nickel iron alloy, but the present invention is not limited thereto. In the deposition process, for the sake of increasing the adhesion between the magnetic element 10 and the substrate, chrome (Cr) is coated as an adhesive layer, nickel-iron (NiFe) is coated as a magnetic layer, and then a chromium (Cr) layer is coated on the magnetic layer for being served as a protective layer to prevent oxidation of the magnetic layer. When the vapor deposition of the magnetic member 10 is completed, the related measurement electrodes 16 can be prepared around the magnetic element 10 according to the actual requirement to transmit the follow-up measurement signals. The signal receiver 20 is disposed around the magnetic element 10 to receive a magnetoresistance signal 105.

As shown in part (A) of FIG. 1, the magnetoresistance signal 105 is correspondingly induced to the magnetic element 10 when the magnetic substance 22 approaches the magnetic element 10, and the presence or absence of the magnetic substance 22 is detected according to the changes of the transmitted magnetoresistance signal 105 so as to achieve the passive detection application of the magnetic substance 22.

As shown in part (B) of FIG. 1, the magnetic device 100 with the three-dimensional wave structure of the present invention further includes a magnetic field controller 30 transmitting a modulation signal 305 to control an external magnetic field so as to excite the arrangement of the magnetic moments of the magnetic element 10 and change the magnetization configuration of the magnetic element 10, and to increase the sensitivity of the magnetoresistance signal 105.

In practice, the modulation signal 305 is able to be adjusted the direction and the intensity of the magnetic field. A magnetic pole region 28 is formed on the three-dimensional wave structure of the magnetic element 22 by the cooperation of three-dimensional wave structure and the modulation signal 305, and the magnetic pole region 28 captures and/or fixes the magnetic substance 22 so as to achieve the positive capturing step of the magnetic substance 22.

To be more precise, when the magnetic element 10 is formed in a linear structure, the magnetic elements 10 are able to be arranged in a matrix. In the detection process, when the magnetic substance 22 contacts different magnetic lines generated by different magnetic elements 10, the signal receiver 20 is served as a position detector and/or a path tracker of the magnetic substance 22 according to different magnetoresistance signals 105 corresponding to the magnetic elements 10 when the magnetic elements 10 are arranged in the matrix, so as to determine the relative position or the motion track of the magnetic substance 22.

Figure 2:
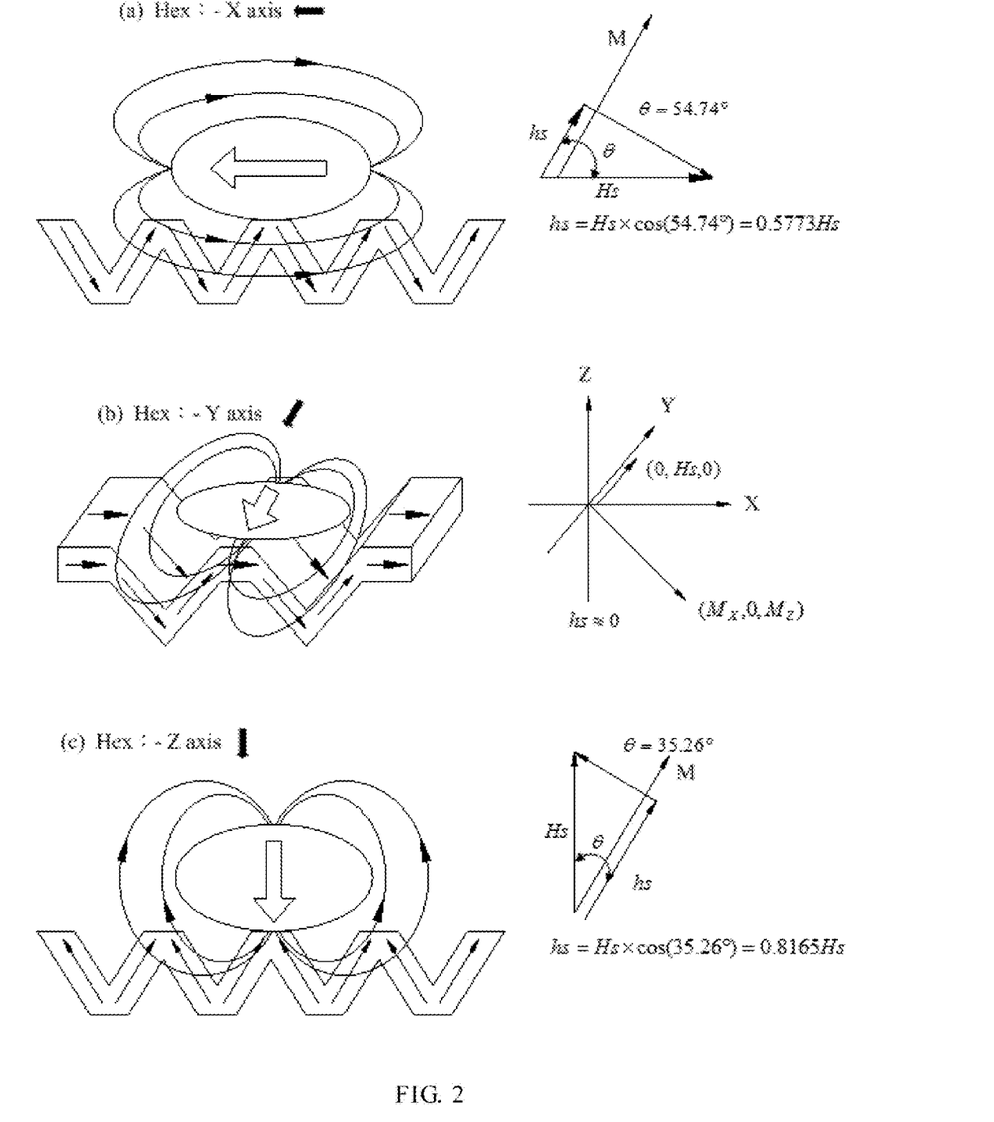
FIG. 2 is a schematic diagram showing the change of a magnetization configuration of a magnetic device with a three-dimensional wave structure of the present invention.

Please concurrently refer to FIG. 1 and FIG. 2, wherein FIG. 2 is a schematic diagram showing the change of a magnetization configuration of a magnetic device with a three-dimensional wave structure of the present invention. As shown in the FIGS., when the magnetic substance 22 is adsorbed to the three-dimensional wave structure 12, the switching field of the magnetic substance 22 becomes significantly larger. The reason is because the internal magnetic moments of the magnetic substance 22 may be arranged along the direction of the external magnetic field to demonstrate the magnetic property when the magnetic substance 22 is affected by the external magnetic field. The stray field produced around the magnetic substance 22 may generate the resisting force to the magnetization occurred in the internal structure of the magnetic element 10, such that the magnetic moments are hard to be switched, and the switching field and the full width at half maximum (FWHM) of the magnetic element 10 thus become larger.

When the magnetic field is parallel to the long axis of the magnetic element 10, the direction is defined as the X-axis direction field. Similarly, when the magnetic field is perpendicular to the long axis of the magnetic element 10, the direction is defined as the Y-axis direction field, and the direction of the magnetic field which is perpendicular to the surface of the magnetic element 10 is defined as the Z-axis direction field. The modulation signal 305 of the magnetic field controller 30 controls the external magnetic field along the X, Y and Z-axis mentioned above.

With the different arrangements of the internal magnetic moments of the magnetic element 10, the stray field has different effective components (hs) on the magnetic moments (M), where the effective components (hs) affect the magnetic moments (M). The sensing variation rate demonstrates between the switching field and the cells become smaller when the magnetic field becomes smaller gradually in the axis-X direction. The magnetic moments are prone to be arranged along the three-dimensional wave structure 12, and then the stray field produced by the magnetic substance 22 may generate the force to resist the magnetization switching in the reversing magnetic field. The arrangement of the stray field of the magnetic substance 22 and the internal magnetic moments of the magnetic element 10 is 54.74° (the etching angle of the lattice plane (100) of the silicon substrate). Hence, the component of the stray field in the direction of the magnetic moments is about 0.5773 times the size of the stray field.

Comparing with the variation range of FWHM, the Y-axis, however, is the hardly-magnetized axis of the magnetic element 10. When the magnetic field becomes smaller gradually, the magnetic moments are arranged along the three-dimensional wave structure 12, and the effective component of the stray field is close to zero in the magnetic moments at this time. Afterwards, the magnetic moments are gradually fixed to the direction parallel to Y-axis, and the effective component of the stray field becomes larger in the direction of the magnetic moments. As FWHM of the magnetic element 10 along Y axis has a larger range and the stray field of the magnetic substance 22 hence has little effect on the magnetic moments, the magnetic element 10 hence has worse sensing efficiency in the Y-axis direction.

Compared to the variation of the switching field in the Z-axis direction, when the magnetic field becomes smaller gradually, the stray field produced by the magnetic substance 22 and the magnetic moments have the arrangement by 35.26°, while the effective component of the stray field is about 0.816 times as great as the stray field in the direction of the magnetic moments. Compared with X-axis and Y-axis, a stronger resisting force may be generated to the magnetization switching in the Z-axis direction.

Figure 3:
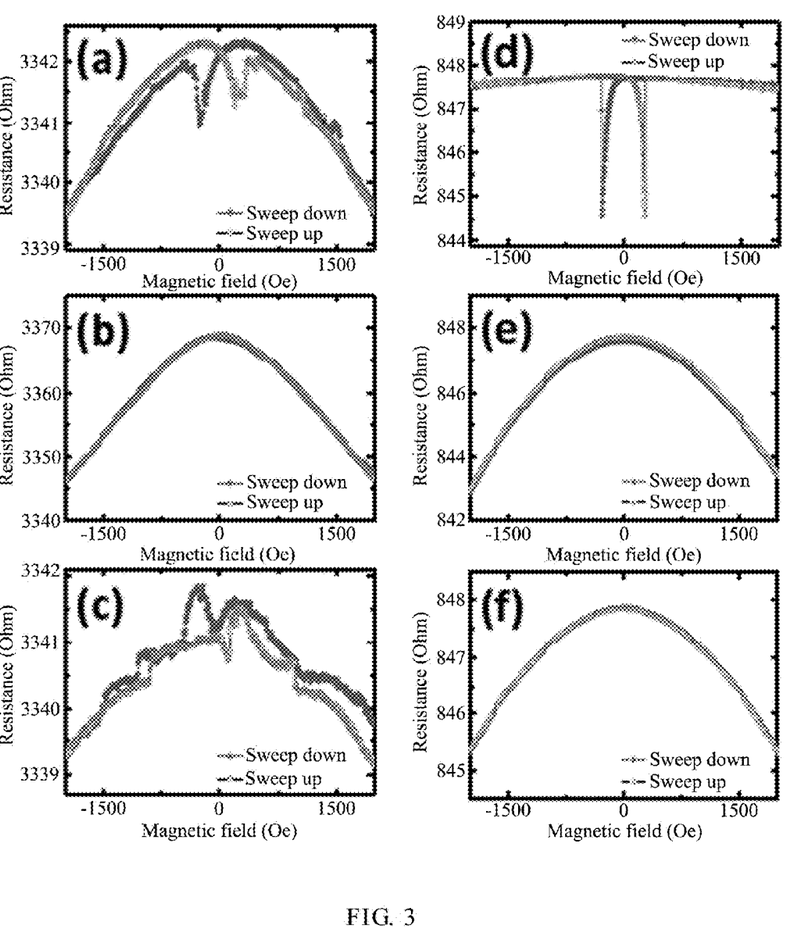
FIG. 3 is a magnetoresistance curve diagram of the first embodiment of a magnetic device with a three-dimensional wave structure of the present invention.

Please refer to FIG. 3 which is a magnetoresistance curve diagram of the first embodiment of a magnetic device with a three-dimensional wave structure of the present invention. The magnetic element 10 is presented as an aspect of magnetic lines in the first embodiment (here, magnetic lines mean magnetic linear structures and do not mean "magnetic field lines"). The magnetic lines made of NiFe are respectively deposited on the planar substrate and the substrate having wave structure. The size of the magnetic lines is of a length of 50 μm, a width of 150 nm and a thickness of 100 nm. The magnetoresistance measurement system is also applied in a magnetic field having a range between ±2000 Oe to measure the change of the magnetoresistance of magnetic lines. Parts of (a)-(c) shown in FIG. 3 are the magnetoresistance curves of the magnetic lines deposited on the substrate having wave structure respectively in external magnetic fields along X, Y, and Z-axes. Parts of (d)-(f) shown in FIG. 3 are the magnetoresistance curves of the magnetic lines deposited on the planar substrate respectively in external magnetic fields along X, Y, and Z-axes.

External Magnetic Field Along X-Axis

Under the action of a large magnetic field, some of the magnetic moments of the magnetic lines of the substrate having wave structure have an included angle of 54.74° with the current direction due to the effect of the wave structure. When the magnetic field becomes smaller gradually, the magnetization configuration inside the wave structure gets a mess, and is prone to be arranged along the three-dimensional wave structure 12. The direction of the arrangement is substantially consistent with that of the current, and the resistance hence becomes larger gradually. When approaching to zero field, the arrangement of the magnetic moments becomes more mess and is parallel to the current or the other non-parallel currents, such that the resistance is lowered and the magnetic switching filed is reversed by 180°, and the resistance has a minimum value when the arrangement of the magnetic moments is perpendicular to the current direction. When the reversing magnetic field becomes larger gradually, the magnetic moments are reversed to parallel to the X-axis direction. Afterwards, a downward peak value also appears when the reversing magnetic field is scanned. Consequently, a complete measurement loop is performed.

The magnetic moments of magnetic lines on the planar substrate are arranged parallel to the X-axis direction. The arrangement of the magnetic moments is parallel to the current direction, so the magnetoresistance is larger. When the magnetic field becomes smaller gradually, the magnetic moments become a mess and the resistance is gradually reduced, and the magnetization switching occurs in the reversing magnetic field. Afterwards, the reversing magnetic field becomes larger gradually, and it is hard for the magnetic lines having smaller diameter to change the magnetization direction of the magnetic moments.

External Magnetic Field Along Y-Axis

The Y-axis is hardly magnetized, so when the magnetic field is reduced, the magnetic moments of the magnetic lines on the substrate having wave structure are prone to be arranged along the wave structure due to the anisotropic effect of the shape of the magnetic moments, and the resistance becomes smaller gradually. The measurement result, however, shows that the magnetic line of 150 nm has little variation rate in the magnetoresistance. The reason is because the scanning range of the magnetic field does not reach to the saturation field of the magnetoresistance, the measured magnetoresistance has little variation. As the magnetic moments parallel to the current direction has the minimum magnetoresistance, the magnetic lines on the planar substrate are prone to be arranged along the long axis of the magnetic film and the resistance becomes larger gradually.

External Magnetic Field Along Z-Axis

It can be found according to the measured result that when the magnetic field is changed from a larger to a smaller, it is more obvious to see the resistance that becomes from smaller to larger as the aspect ratio of the magnetic lines becomes larger gradually. Namely, the thinner line diameter the magnetic lines have, the more obvious the property of the magnetic lines becomes. As it is not easy for the magnetic lines having thinner diameter to change the magnetization direction, the magnetization direction can be reversed as a whole in a larger reversing magnetic field. The variation rate of the magnetoresistance becomes from smaller to larger according to the diameter of the magnetic lines.

The magnetic moments of the magnetic lines on the planar substrate are perpendicular to the current direction and have the minimal magnetoresistance. When the magnetic field becomes smaller, the magnetic moments are arranged along the long axis of the magnetic film, and the magnetoresistance becomes larger gradually. It is difficult to change the magnetization direction of the magnetic moments, so FWHM along the Z-axis is greater than that along the Y-axis.

Figure 4:
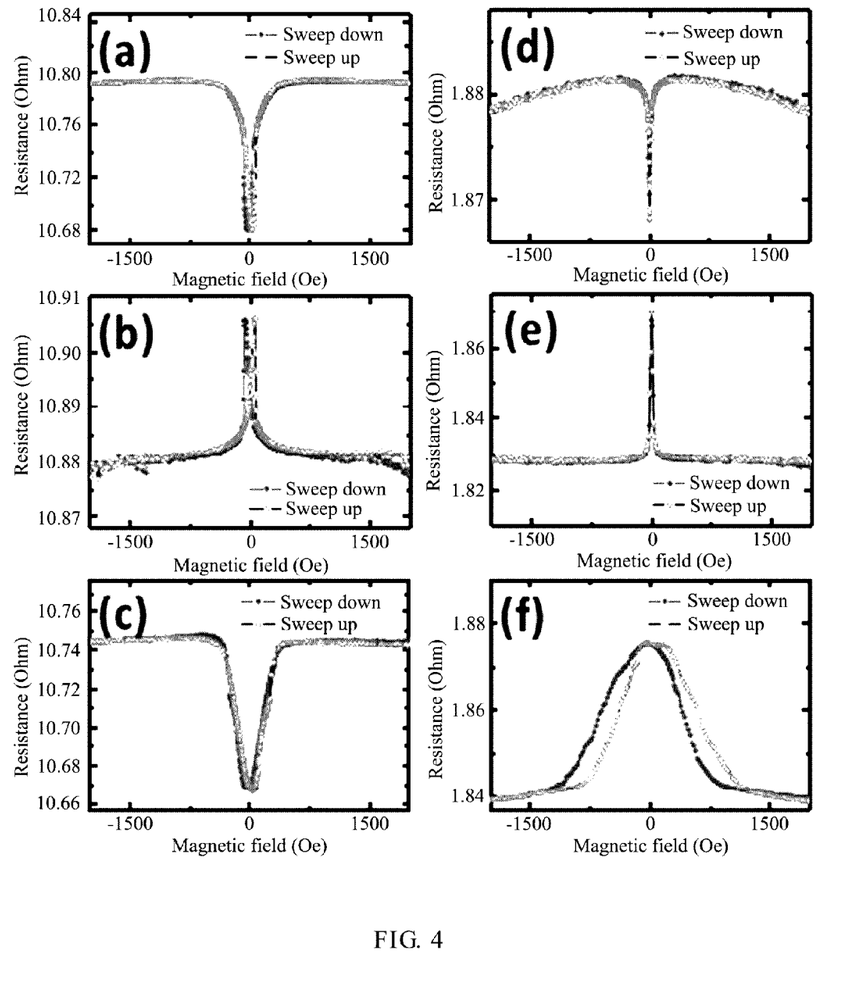
FIG. 4 is a magnetoresistance curve diagram of the second embodiment of a magnetic device with a three-dimensional wave structure of the present invention.

Please refer to FIG. 4 which is a magnetoresistance curve diagram of the second embodiment of a magnetic device with a three-dimensional wave structure of the present invention. The magnetic element 10 is presented by an aspect of a magnetic thin film in the second embodiment. Similarly, the magnetic thin films having a length of 60 μm, a width of 50 μm and a thickness of 100 nm are respectively deposited on the substrate having wave structure and the planar substrate in order to explore the effect of the geometry characteristics on the magnetic switching field. Parts of (a)-(c) shown in FIG. 4 are the magnetoresistance curves of the magnetic thin films deposited on the substrate having wave structure respectively in external magnetic fields along X, Y, and Z-axes. Parts of (d)-(f) shown in FIG. 4 are the magnetoresistance curves of the magnetic thin films deposited on the planar substrate respectively in external magnetic fields along X, Y, and Z-axes.

Compared with the magnetic lines, the aspect ratio of the structure of the magnetic thin films on the substrate having the wave structure are smaller such that the component is smaller in the Z-axis direction when the magnetic moments are arranged in the direction of the wave structure. Although the variation of the magnetoresistance has little effect, the detection of the anisotropic magnetoresistance of the magnetic thin films on the substrate having the wave structure is better than that on the planar substrate.

By observing the magnetoresistance curves of the magnetic thin film at any directions on the planar substrate, it can be found that the reversing magnetic field and FWHM do not have regular pattern. The reason can be inferred that the planar magnetic thin film has the micron level, and the arrangement of the internal magnetic moments is complicated and may be separated into plural magnetic regions. Consequently, it may become harder for the variation of the magnetoresistance to be controlled, and the reproducibility of the measurement is degraded. When measuring in the Z-axis direction particularly, since the thickness of the magnetic thin film is about $\frac{1}{600}$-$\frac{1}{500}$ times as long as the length or the width thereof, it is easy for the measured result to be influenced by components in other axial direction, which causes the difficulty for measurement and affects the precision of the experiment.

As the experimental results mentioned above, it can be found that no matter in the aspects of magnetic lines or magnetic thin films, the detection sensitivity of the magnetic element 10 on the substrate having wave structure is better than that on the planar substrate.

To be more precise, as far as the conventional magnetic detector having two-dimensional structure is concerned, the magnetic device 100 with the three-dimensional wave structure of the present invention applies the magnetic element 10 having the three-dimensional wave structure 12 to cooperate with the magnetoresistance signal 105 to provide multi-dimensional detection directions so as to promote the efficiency and precision of the detection. In addition, the three-dimensional wave structure 12 is applied to increase the magnetic component in the Z-axis to enhance the resolution of the magnetoresistance signal 105.

In practice, the magnetic device 100 with the three-dimensional wave structure of the present invention further includes a microfluid generator providing a microfluid. When the magnetic substance 22 is fixed to the magnetic pole region 28, a magnetic file controller 30 modulating the external magnetic field cooperates with a washing function of the microfluid so as to be served as a magnetic substance separating system. Hence, not only the requirement of the magnetic field can be reduced, but separation by steps can be realized to achieve the objectives of separating the magnetically-tagged object from the non-magnetically-tagged object.

Furthermore, the magnetic device 100 with the three-dimensional wave structure of the present invention may include a flow channel unit. The present device is connected to the flow channel unit, and the magnetic element 10 is able to detect the presence of the magnetic substances, cells, or biomolecules. Therefore, by detecting the magnetic substance 22 flowing through the flow channel unit, the amount of the flowing cells or biomolecules can be calculated. Therefore, the magnetic device 100 with the three-dimensional wave structure can be served as a magnetic counting system.

Figure 5:
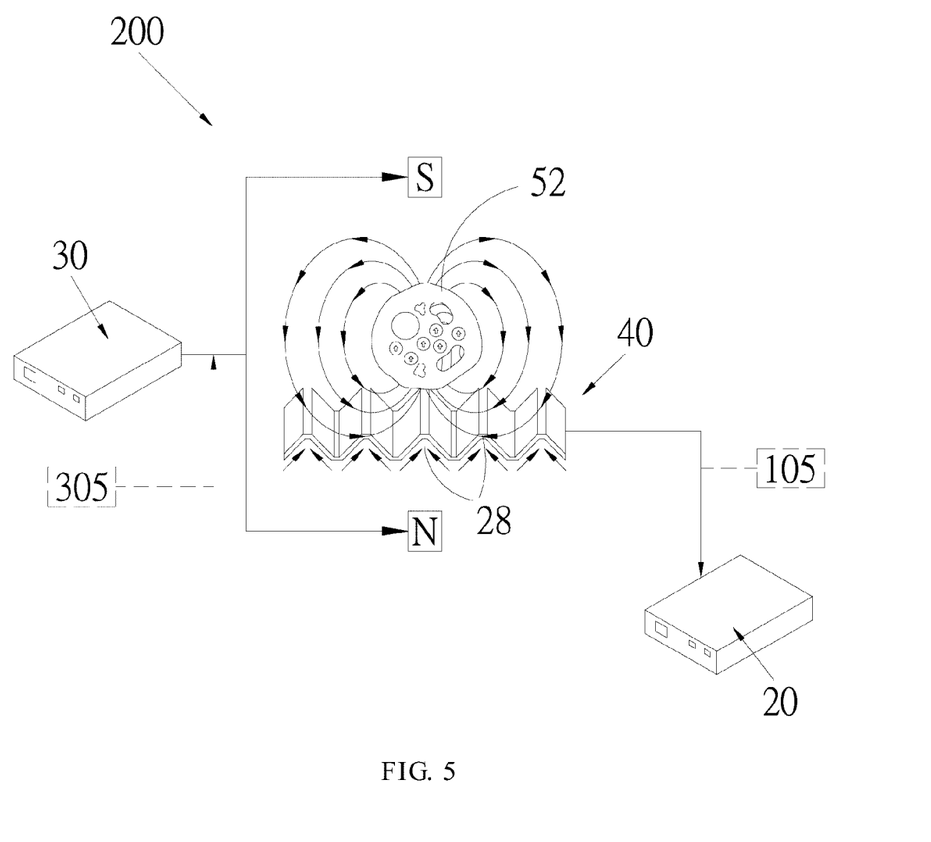
FIG. 5 is a schematic diagram of a magnetic biomedical detection device of the present invention.

Please refer to FIG. 5 which is a schematic diagram of a magnetic biomedical detection device of the present invention. As shown in FIG. 5, a magnetic biomedical detection device 200 includes a magnetic detection thin film 40, a signal receiver 20 and the magnetic field controller 30. The magnetic detection thin film 40 having large area is applied to cooperate with adequate modulation signal 305 to modulate the axial direction of the external magnetic field. The anisotropic magnetoresistance forms a magnetic pole region 28 in the characteristic region of the three-dimensional wave structure 12, and the magnetic field intensity of the magnetic pole region 28 is slightly higher than the surrounding magnetic fields. Hence, the magnetic pole region 28 performs better magnetic adsorption for a magnetic biomedical substance 52 so as to actively capture the magnetic biomedical substance 52.

In practice, the magnetic biomedical substance 52 includes a magnetically-tagged biomolecule, a magnetic particle, a magnetic cell, a magnetic molecular structure, a magnetic fluid or a combination thereof. In the practical application, the magnetic biomedical substance 52 is arranged in a pattern by modulating the magnetic field of the magnetic pole region 28 for contributing to the follow-up detection.

Figure 6:
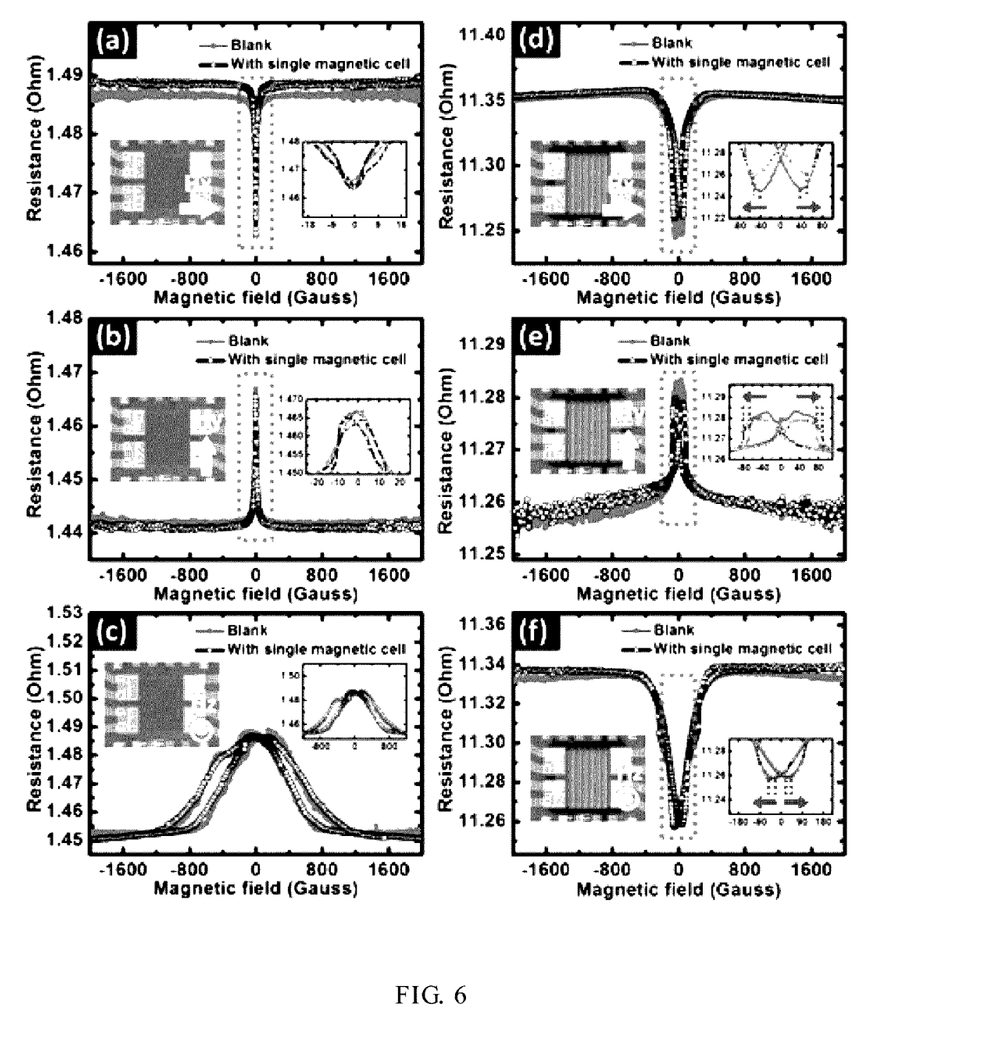
FIG. 6 is a magnetoresistance curve diagram of the first embodiment of a magnetic biomedical detection device of the present invention.

Please refer to FIG. 5 and FIG. 6 together. FIG. 6 is a magnetoresistance curve diagram of the first embodiment of a magnetic biomedical detection device of the present invention. Parts of (a)-(c) shown in FIG. 6 are the magnetoresistance curves of the planar thin film in the X, Y and Z-axis. Parts of (d)-(f) shown in FIG. 6 are the magnetoresistance curves of the magnetic detection thin film 40 in the X, Y and Z-axis. As shown in FIG. 6, when the magnetic biomedical substance 52 contacts with the planar thin film on the planar substrate, the variation of each feature (switching field and FWHM) of the magnetoresistance curves does not have obvious regularity, and the reproducibility is bad. In contrast, when the magnetic biomedical substance 52 contacts with the magnetic detection thin film 40, the switching field in the X and Z-axis direction becomes larger, and FWHM in the Y-axis direction also becomes larger. The results prove that the magnetic detection thin film 40 disclosed in the present invention has better detection sensitivity for detecting the magnetic biomedical substance 52.

Therefore, by measuring variation of the magnetic detection thin film 40, the presence and absence of the magnetic cells and magnetic fluids can be detected, where the Z-axis direction field is applied to such structure to obtain the optimal sensing effect. The variation rate of sensing the magnetic cells and the magnetic fluids in the Z-axis direction may be up to 34.19% and 117.72%, respectively. The sensing efficiency of the magnetic cells and the magnetic fluids in the X-axis direction are respectively 27.28% and 52.92%, and the sensing efficiency of the magnetic cells and the magnetic fluids in the Y-axis direction are respectively 17.86% and 46.19%

Figure 7:
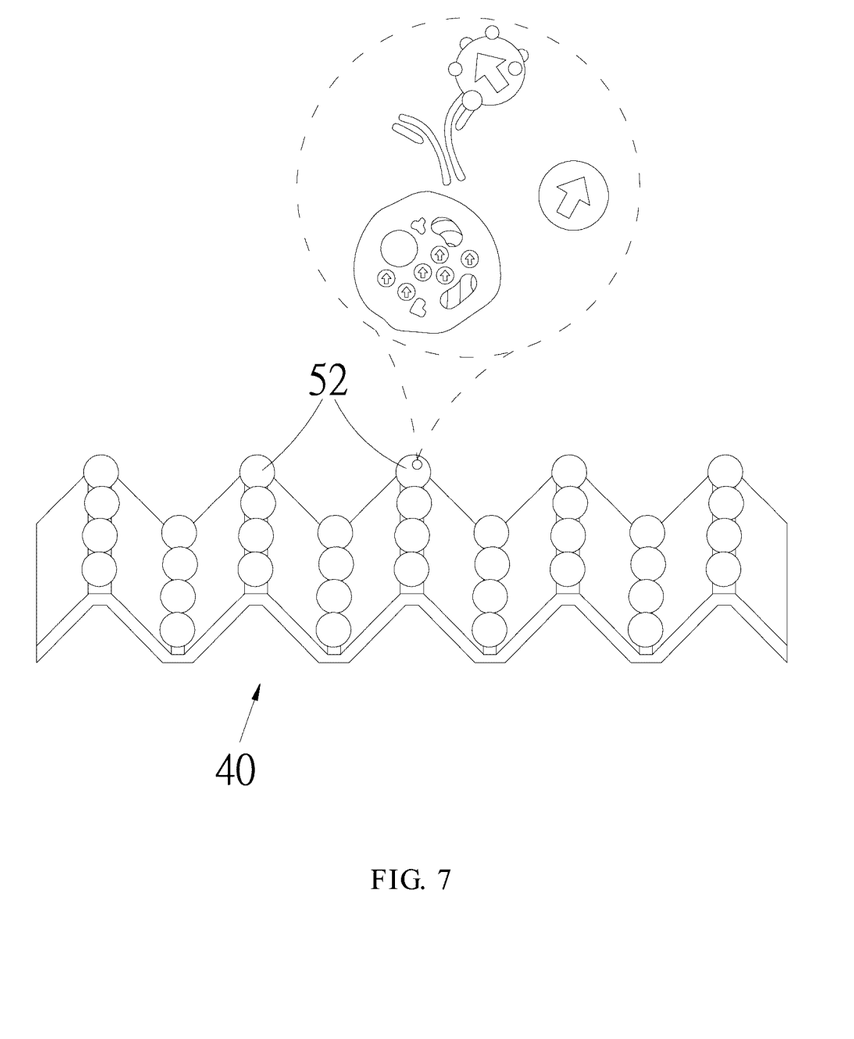
FIG. 7 is a schematic diagram of a patterned arrangement of a magnetic biomedical detection device of the present invention.

Please refer to FIG. 7 which is a schematic diagram of a patterned arrangement of a magnetic biomedical detection device of the present invention. Applying the magnetic detection thin film 40 to cooperate with the magnetization configuration is able to respectively arrange the magnetic biomedical substance 52 such as various cells or biomolecules at the tops and gaps of the magnetic detection thin film 40 so as to achieve the objective of patterning the magnetic biomedical substance 52.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A magnetic device with a three-dimensional wave structure, comprising:
    at least one magnetic element comprising a nano/micro structure having magnetic anisotropy and the at least one magnetic element disposed on a substrate with a three-dimensional wave structure, wherein a magnetic substance correspondingly induces a magnetoresistance signal to the at least one magnetic element when the magnetic substance approaches the at least one magnetic element;
    a measurement electrode disposed around the at least one magnetic element; and
    a signal receiver disposed around the at least one magnetic element and electrically connected to the at least one magnetic element through the measurement electrode to receive the magnetoresistance signal corresponding to the at least one magnetic element.

2. The magnetic device with the three-dimensional wave structure of claim 1, further comprising: a magnetic field controller transmitting a modulation signal to control an external magnetic field.

3. The magnetic device with the three-dimensional wave structure of claim 2, wherein a magnetic pole region is formed in the three-dimensional wave structure of the at least one magnetic element by the three-dimensional wave structure according to the modulation signal, and the magnetic pole region captures or fixes the magnetic substance.

4. The magnetic device with the three-dimensional wave structure of claim 3, further comprising a microfluid generator providing a microfluid, wherein when the magnetic substance is fixed to the magnetic pole region, the external magnetic field performs a magnetic field modulation and cooperates with a washing function of the microfluid to be served as a magnetic substance separating system.

5. The magnetic device with the three-dimensional wave structure of claim 2, wherein the external magnetic field is applied in an arbitrary axial direction based on an actual requirement to reinforce detection intensity and a detection freedom of the magnetoresistance signal.

6. The magnetic device with the three-dimensional wave structure of claim 2, wherein the modulation signal changes an applied direction of the external magnetic field to change a magnetization configuration of the at least one magnetic element to arrange the magnetic substance in a pattern.

7. The magnetic device with the three-dimensional wave structure of claim 1, further comprising a flow channel unit connected to the magnetic device with the three-dimensional wave structure to detect the magnetic substance flowing through the flow channel unit to be served as a magnetic counting system.

8. The magnetic device with the three-dimensional wave structure of claim 1, wherein the signal receiver is served as a position detector or a path tracker of the magnetic substance according to different magnetoresistance signals corresponding to the at least one magnetic element when the at least one magnetic element is arranged in a matrix.

9. The magnetic device with the three-dimensional wave structure of claim 1, wherein the magnetic substance comprises a magnetically-tagged biomolecule, a magnetic particle, a magnetic cell, a magnetic molecular structure, a magnetic fluid or a combination thereof.

10. The magnetic device with the three-dimensional wave structure of claim 1, wherein the nano/micro structure comprises a linear structure, a thin film structure, a ring structure, a circular structure, an Antidot, an elliptic structure, a spin valve structure or a combination thereof.

* * * * *